United States Patent [19]  [11] 4,076,594
Buelow et al. [45] Feb. 28, 1978

[54] PURIFICATION OF FORMIC ACID BY EXTRACTIVE DISTILLATION

[75] Inventors: Horst Buelow, Frankenthal; Heinz Hohenschutz, Mannheim; Johannes E. Schmidt; Werner Sachsze, both of Ludwigshafen, all of Germany

[73] Assignee: BASF Aktiengesellschaft, Ludwigshafen am Rhine, Germany

[21] Appl. No.: 729,858

[22] Filed: Oct. 4, 1976

[30] Foreign Application Priority Data

Oct. 11, 1975 Germany .............................. 2545730

[51] Int. Cl.² ........................ B01D 3/40; C07C 51/44
[52] U.S. Cl. ..................................... 203/15; 203/58; 203/84; 260/542
[58] Field of Search ...................... 203/15, 58, 16, 38, 203/84; 260/542, 541

[56] References Cited

U.S. PATENT DOCUMENTS

| 1,919,850 | 7/1933 | Luscher | 260/542 |
| 2,034,332 | 3/1936 | Dragendorff et al. | 260/542 |
| 2,313,386 | 3/1943 | Levesque | 260/541 |
| 2,357,412 | 9/1944 | Levesque | 203/15 |
| 3,434,936 | 3/1969 | Luther | 260/58 |
| 3,673,081 | 6/1972 | Preusser et al. | 203/58 |
| 3,878,241 | 4/1975 | Muller | 260/542 |
| 3,983,010 | 9/1976 | Rauch et al. | 260/542 |

Primary Examiner—Wilbur L. Bascomb, Jr.
Attorney, Agent, or Firm—Keil, Thompson & Shurtleff

[57] ABSTRACT

Formic acid is purified by extractive distillation of its aqueous solutions using a basic extractant, followed by distillation of the bottom mixture first obtained, the extractant used being N-formylmorpholine.

4 Claims, No Drawings

PURIFICATION OF FORMIC ACID BY EXTRACTIVE DISTILLATION

The present invention relates to a new process for the purification of formic acid by extractive distillation.

In the industrial syntheses of formic acid, for example by reacting methanol and carbon monoxide and hydrolyzing the methyl formate first formed, aqueous solutions containing from about 20 to 50% of acid are always obtained. When worked up by distillation, these solutions give an azeotrope, so that the formic acid cannot be obtained from them directly in an anhydrous or substantially anhydrous form.

Water is conventionally distilled from such solutions by using entraining agents, e.g. ethers, esters and ketones. However, such processes have a high energy consumption, so that extractive distillation, which is also a conventional process, is generally preferred. In extractive distillation, the formic acid is extracted from the aqueous vapor phase by means of a basic extractant introduced in counter-current, and is transported to the bottom of the column. A mixture of the extractant and of formic acid, loosely bonded to the extractant as a salt, is obtained. When this mixture is heated, the formic acid is liberated and can be distilled off in a pure form.

According to the process of German Laid-Open Application DOS 2,201,827, 1,2-di-n-morpholylethane is used as an extractant for the extractive distillation of an aqueous mixture which in the main contains acetic acid, and all the acids, including formic acid, pass to the bottom of the column. It is true that it is pointed out, in this context, that the formic acid may undergo thermal decomposition, and that this disadvantage can be avoided by choosing suitable process conditions, However, the application of this process to the purification of substantial amounts of formic acid does not prove satisfactory, because the temperatures required for scission of the formic acid adduct are such that the formic acid itself also undergoes significant decomposition. Furthermore, 1,2-di-N-morpholylethane is solid at normal temperatures, which produces technological difficulties, especially in the event of a breakdown.

It is an object of the present invention to obtain pure formic acid from its aqueous solutions by extractive distillation, using more suitable extractants than those employed hitherto, without causing partial decomposition of the formic acid and without requiring special apparatus or abnormal energy consumption.

We have found that this object is achieved and that formic acid is obtained in a pure form by extractive distillation of its aqueous solutions by means of a basic extractant, followed by distillation of the bottom mixture first obtained, if N-formylmorpholine is used as the extractant.

In accordance with the function it performs, the N-formylmorpholine is employed in at least stoichiometric amounts, but preferably in up to 0.2 molar excess, based on formic acid. In the continuous method, which is used almost exclusively in industry, and in which the extractant is recycled, the amount of N-formylmorpholine depends — as can easily be calculated — on the output and constructional details of the installation, but it is advantageous to have available from 1 to 1.2 moles of the extractant per mole of formic acid in the gas phase.

In this embodiment, the procedure generally followed is to vaporize the aqueous formic acid at from 50° to 110° C and from 50 to 760, preferably from 100 to 200, mm Hg, and to pass these vapors into the middle or lower zone of the extraction column. The extractant is passed in at the top, in counter-current, takes up the formic acid and arrives, together with the latter, at the bottom, which is at from 80° to 125° C. It is also possible first to vaporize the aqueous formic acid in the extraction column. The water which escapes at the top of the column only contains small residual amounts of organic substance and can therefore be treated in the conventional manner. The extractant and the formic acid bonded thereto are fed into the middle zone of a second column, from which the pure formic acid is taken off at the top, at from 45° to 50° C (top temperature) and from 55 to 65 mm Hg, whilst the extractant which remains as the bottom product is returned to the first column. Suitable extraction columns are, in particular, bubble-cap columns with from 15 to 30 actual trays (the aqueous formic acid being introduced at about the level of the 4th to 6th tray), whilst, because of the relatively low volatility of the extractant, a short packed column suffices for the distillation of pure formic acid.

Apart from the measure taken in accordance with the invention, the process may be carried out by conventional methods and thus requires no further explanation. If high-boiling impurities progressively accumulate in the extractant, the latter is advantageously purified by distillation, Such a distillation can also form part of the recycling system.

As has been shown by several sets of experiments, heating at 160° C is necessary in order to drive off 90% of the formic acid bonded to the extractant if 1,2-di-N-morpholylethane is used as the latter, whilst a temperature of 150° C suffices in the case of the extractant according to the invention. In contrast to the conventional process, there are no significant losses of formic acid due to decomposition, and furthermore the energy requirements are also lower.

EXAMPLE

Using an experimental unit consisting essentially of a bubble-cap tray column (diameter 6 cm, height 1.5 m) with 25 trays, and an 0.5 m high stripping column filled with Raschig rings, 225 g per hour of a 75% strength aqueous formic acid solution were worked up, with 515 g/hour of N-formylmorpholine as the extractant (corresponding to 1.17 mole of extractant per mole of formic acid). The bottom temperature was 115° C; the solution was added at the level of the 6th tray, counting from the bottom.

The water was separated off virtually quantitatively, and free from organic substances, whilst the N-formylmorpholine/formic acid mixture was fed to the stripping column, where it was separated into its components at 150° C and 60 mm Hg.

The yield of 99% strength formic acid was 99.5%.

A 50% strength formic acid was dehydrated by the same process.

We claim:

1. A process for recovery of formic acid from its aqueous solution which comprises vaporizing said aqueous solution of formic acid, passing the vapor into the middle zone or a lower zone of a distillation column and passing a liquid basic extractant into the top of said column, distilling off water from said column, extracting the formic acid in said extractant as it passes downwardly through the column, the extractant forming a liquid bottoms product, using N-formylmorpholine as the extractant, removing the bottoms product containing the formic acid from said column, and distilling off formic acid from said removed bottoms product in a second distillation column.

2. A process as claimed in claim 1, wherein the aqueous solution contains 20 to 50% by weight of formic acid and is obtained in the synthesis of formic acid by reaction of carbon monoxide and methanol followed by hydrolysis of the resulting methyl formate.

3. A process as claimed in claim 1, wherein the N-formylmorpholine is employed in an excess of up to 0.2 molar, based on formic acid.

4. A process as claimed in claim 1, which process is carried out continually by vaporizing said aqueous solution of formic acid at 50 to 110° C and 50 to 760 mm Hg and passing the vapor into said middle or lower zone of said column while passing N-formylmorpholine into the top of said column in liquid form and in countercurrent flow to the rising vapors in said column, the bottoms product in said column attaining a temperature of 80° to 125° C, and the distillation in said second column being carried out at a top temperature of 45° to 50° C and a pressure of 55 to 65 mm Hg.

* * * * *